US012636080B2

(12) United States Patent
Takata et al.

(10) Patent No.: US 12,636,080 B2
(45) **Date of Patent: *May 26, 2026**

(54) LASER SCANNING METHOD, LASER IRRADIATION DEVICE, AND LASER TREATMENT SYSTEM

(71) Applicant: OLYMPUS CORPORATION, Tokyo (JP)

(72) Inventors: Yuhei Takata, Tokyo (JP); Takumi Hayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 309 days.

This patent is subject to a terminal disclaimer.

(21) Appl. No.: 18/242,112

(22) Filed: Sep. 5, 2023

(65) Prior Publication Data

US 2023/0404669 A1     Dec. 21, 2023

Related U.S. Application Data

(63) Continuation of application No. PCT/JP2021/009531, filed on Mar. 10, 2021.

(51) Int. Cl.
*A61B 18/26*          (2006.01)
*A61B 1/06*           (2006.01)
(Continued)

(52) U.S. Cl.
CPC ............ *A61B 18/26* (2013.01); *A61B 1/0655* (2022.02); *A61B 1/07* (2013.01); *G02B 26/103* (2013.01);
(Continued)

(58) Field of Classification Search
CPC ......... A61B 18/26; A61B 1/0655; A61B 1/07; A61B 2018/00732; A61B 2018/00773; A61B 2018/263; G02B 26/103
See application file for complete search history.

(56) References Cited

U.S. PATENT DOCUMENTS 5,254,114 A     10/1993   Reed, Jr. et al.
5,632,739 A     5/1997    Anderson et al.
(Continued)

FOREIGN PATENT DOCUMENTS

EP        0 529 823 A1      3/1993
EP        3791821 A1 *      3/2021    ........... A61N 5/0624
(Continued)

OTHER PUBLICATIONS

US Office Action dated Aug. 5, 2025 received in U.S. Appl. No. 18/242,115.
(Continued)

*Primary Examiner* — Shirley X Jian
(74) *Attorney, Agent, or Firm* — Scully, Scott, Murphy & Presser, P.C.

(57)          ABSTRACT

A laser scanning method that is a method for scanning a laser beam emitted from a distal end of an optical fiber in a liquid medium. The laser scanning method includes emission of a pulsed laser beam from the distal end in the medium, wherein the emission of the pulsed laser beam includes: generating a bubble that is to come into contact with the distal end and an operation member by means of the laser beam emitted from the distal end, the operation member being disposed only at one side of the distal end in a radial direction of the optical fiber; and contracting the bubble by stopping the emission of the laser beam from the distal end.

20 Claims, 17 Drawing Sheets

(51) Int. Cl.
    *A61B 1/07*          (2006.01)
    *G02B 26/10*       (2006.01)
    *A61B 18/00*       (2006.01)

(52) U.S. Cl.
    CPC ............... *A61B 2018/00732* (2013.01); *A61B 2018/00773* (2013.01); *A61B 2018/263* (2013.01)

(56) References Cited

U.S. PATENT DOCUMENTS

| | | | |
|---|---|---|---|
| 5,776,127 | A | 7/1998 | Anderson et al. |
| 6,538,739 | B1 | 3/2003 | Visuri et al. |
| 2015/0238215 | A1* | 8/2015 | Kojima .............. A61B 17/3203 606/167 |
| 2015/0342678 | A1* | 12/2015 | Deladurantaye ........ A61F 9/008 606/5 |
| 2017/0042618 | A1 | 2/2017 | Brown |
| 2018/0064323 | A1 | 3/2018 | Fujinuma |
| 2021/0069756 | A1* | 3/2021 | Lukac .................. A61N 5/0624 |

FOREIGN PATENT DOCUMENTS

| | | | |
|---|---|---|---|
| JP | H06-261910 | A | 9/1994 |
| JP | 2001-517805 | A | 10/2001 |
| JP | 2015-123106 | A | 7/2015 |
| WO | 1996/028998 | A2 | 9/1996 |
| WO | 1999/016366 | A1 | 4/1999 |

OTHER PUBLICATIONS

International Search Report dated Apr. 27, 2021 received in PCT/JP2021/009531.

International Search Report dated May 17, 2022 received in PCT/JP2022/008752.

Ayton A. Hall, et al.,"Thulium fiber laser stone dusting using an automated, vibrating optical fiber", SPIE BIOS, 2019, San Francisco, California, United States, Proceedings vol. 10852, Therapeutics and Diagnostics in Urology 2019;108520C-1 to 11(2019), Retrieved from the Internet. URL:https://www.spiedigitallibrary.org/conference-proceedings-of-spie/10852/108520C/Thulium-fiber-laser-stone-dusting-using-an-automated-vibrating-optical/10.1117/12.2506789.short?SSO=1.

Cameron M. Lee, et al., "Scanning fiber endoscopy with highly flexible, 1-mm catheterscopes for wide-field, full-color maging", Journal of Biophotonics, 3(5-6)pp. 385-407, (Author manuscript; available in PMC) Retrieved from the Internet.URL:https://www.ncbi.nlm.nih.gov/pmc/articles/PMC3163080.

\* cited by examiner

FREQUENCY (Hz)

AMPLITUDE OF OPTICAL FIBER

FIG. 10B

LASER SCANNING METHOD, LASER IRRADIATION DEVICE, AND LASER TREATMENT SYSTEM

CROSS-REFERENCE TO RELATED APPLICATIONS

This is a continuation of International Application PCT/JP2021/009531, with an international filing date of Mar. 10, 2021, which is hereby incorporated by reference herein in its entirety.

TECHNICAL FIELD

The present invention relates to laser scanning methods, laser irradiation devices, and laser treatment systems.

BACKGROUND ART

A known medical device in the related art scans a laser beam for treatment or imaging (e.g., see Non Patent Literatures 1 and 2). In Non Patent Literatures 1 and 2, an optical fiber is vibrated by an actuator to scan a laser beam emitted from the distal end of the optical fiber. In detail, Non Patent Literature 1 uses an electromagnetic actuator having a magnet bead fixed to the optical fiber and a solenoid disposed around the magnet bead. Non Patent Literature 2 uses a piezoelectric actuator having a piezoelectric element fixed to the optical fiber.

CITATION LIST

Non Patent Literature

{Non Patent Literature 1}
  Layton A. Hall, two others, "Thulium fiber laser stone dusting using an automated, vibrating optical fiber.", Proceedings, Volume 10852, Therapeutics and Diagnostics in Urology 2019, 108520C, Feb. 26, 2019
{Non Patent Literature 2}
  Lee, C. M., four others, "Scanning fiber endoscopy with highly flexible, 1 mm catheterscopes for wide-field, full-color imaging.", Journal of Biophotonics, Jun. 3, 2010, Volume 3, pp. 385-407

SUMMARY OF INVENTION

A first aspect of the present invention provides a laser scanning method for scanning a laser beam emitted from a distal end of an optical fiber in a liquid medium, the laser scanning method including emission of a pulsed laser beam from the distal end of the optical fiber in the liquid medium, wherein the emission of the pulsed laser beam includes: generating a bubble that is to come into contact with the distal end of the optical fiber and an operation member by means of the laser beam emitted from the distal end of the optical fiber, the operation member being disposed only at one side of the distal end of the optical fiber in a radial direction of the optical fiber; contracting the bubble by stopping the emission of the laser beam from the distal end of the optical fiber; and causing the optical fiber to vibrate by means of causing a contraction force to act on the optical fiber and by means of causing the optical fiber to move toward a side opposite from the optical member by a restoring force of the optical fiber when the bubble vanishes and the contraction force dissipates.

A second aspect of the present invention provides a laser irradiation device including: a laser oscillator that supplies a pulsed laser beam to an optical fiber to be emitted from a distal end of the optical fiber in a liquid medium; and a controller configured to control emission of the pulsed laser beam by the laser oscillator, wherein the controller is configured to repeatedly conduct supply of the laser beam and stoppage of the laser beam, wherein timing of the supply and the stoppage is set to: generate a bubble at the distal end of the optical fiber by emitting the laser beam from the distal end of the optical fiber; contract the bubble by stopping the emission of the laser beam from the distal end of the optical fiber; and cause the optical fiber to vibrate by means of causing a contraction force to act on a space between the optical fiber and an operation member located adjacent to the optical fiber to move the optical fiber close to the operation member and by means of causing the optical fiber to move toward a side opposite from the optical member by a restoring force of the optical fiber when the bubble vanishes and the contraction force dissipates.

A third aspect of the present invention provides a laser treatment system including: a laser fiber to be positioned in a liquid medium; a laser oscillator that supplies a pulsed laser beam to the optical fiber to be emitted from a distal end of the optical fiber; and a controller configured to control emission of the pulsed laser beam by the laser oscillator, wherein the controller is configured to repeatedly conduct supply of the laser beam and stoppage of the laser beam, wherein timing of the supply and the stoppage is set to:
  generate a bubble at the distal end of the optical fiber by emitting the laser beam from the distal end of the optical fiber; contract the bubble by stopping the emission of the laser beam from the distal end of the optical fiber; and cause the optical fiber to vibrate by means of causing a contraction force to act on a space between the optical fiber and an operation member located adjacent to the optical fiber to move the optical fiber close to the operation member and by means of causing the optical fiber to move toward a side opposite from the optical member by a restoring force of the optical fiber when the bubble vanishes and the contraction force dissipates.

Advantageous Effects of Invention

The present invention is advantageous in that a laser beam can be scanned in a liquid medium without having to add an actuator for driving an optical fiber to the optical fiber and without increasing the power consumption.

BRIEF DESCRIPTION OF DRAWINGS

FIG. 10B illustrates an overall configuration of a laser treatment system according to another embodiment of the present invention.

DESCRIPTION OF EMBODIMENTS

A laser scanning method, a laser irradiation device, and a laser treatment system according to an embodiment of the present invention will be described below with reference to the drawings.

Figure 1:
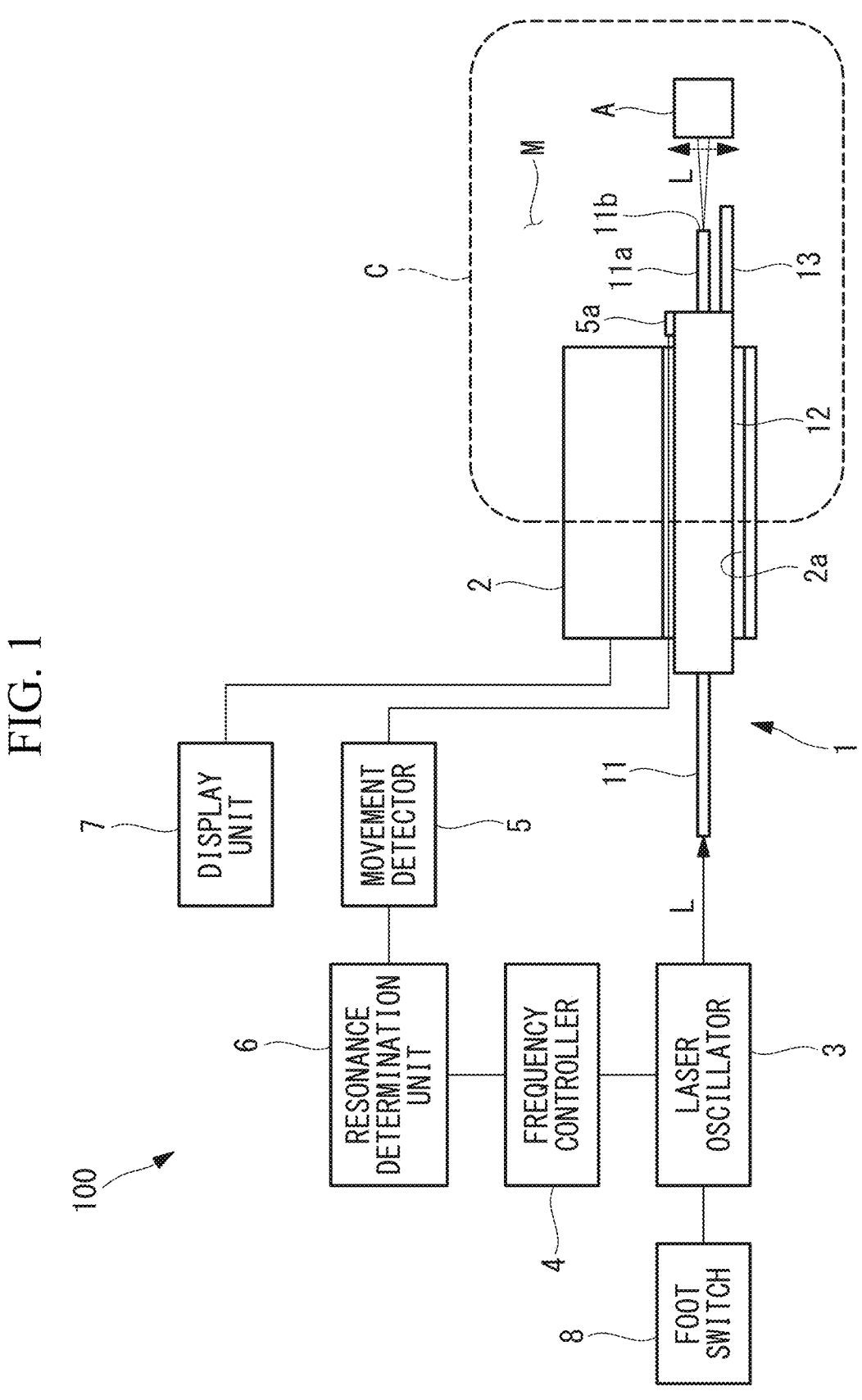
FIG. 1 illustrates an overall configuration of a laser treatment system according to an embodiment of the present invention.

As shown in FIG. 1, a laser treatment system 100 according to this embodiment treats a treatment target A by using a laser beam L. The laser treatment system 100 includes a laser irradiation device 1, an endoscope 2, a laser oscillator 3, a frequency controller 4, a movement detector 5, a resonance determination unit 6, and a display unit 7.

The endoscope 2 is a rigid or flexible ureteroscope. The endoscope 2 has a surgical-tool channel 2a extending longitudinally through the endoscope 2.

Figure 2:
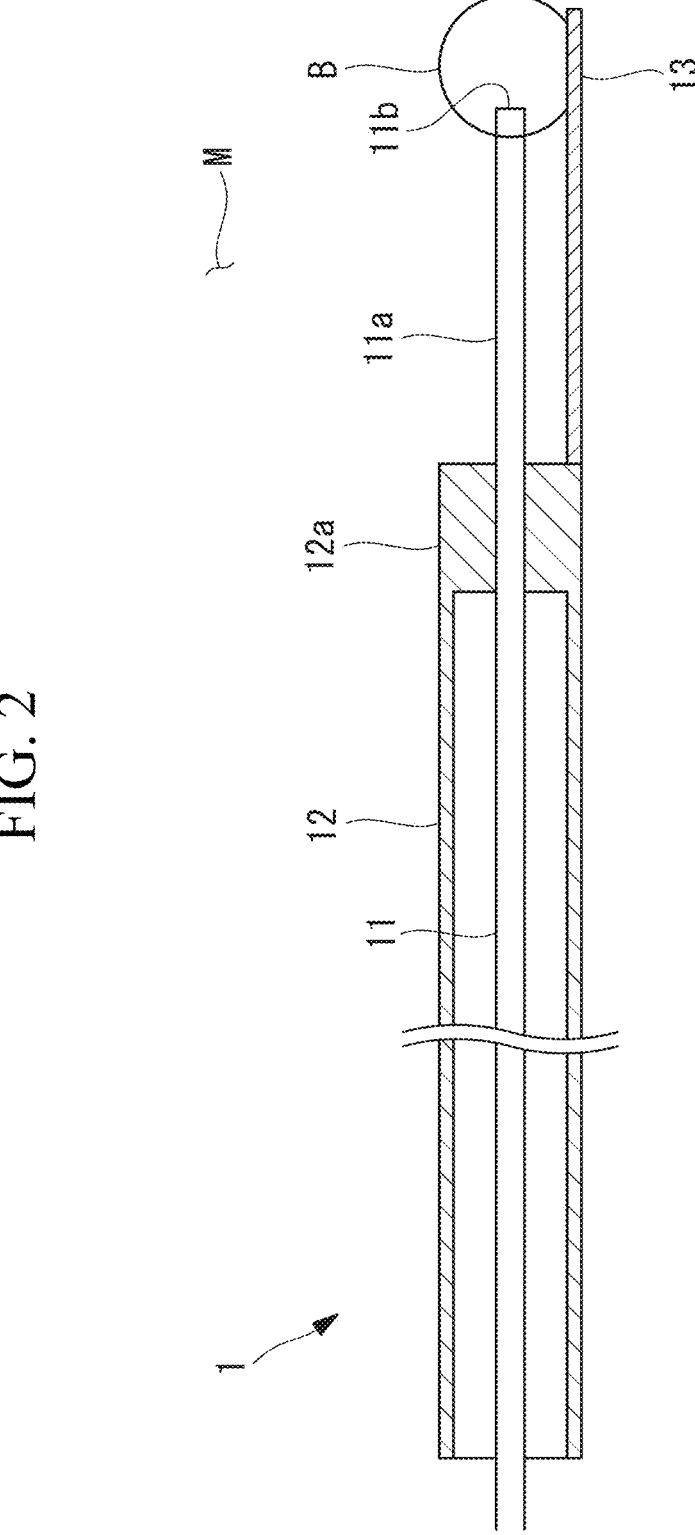
FIG. 2 illustrates a configuration of a laser irradiation device according to an embodiment of the present invention.

As shown in FIG. 2, the laser irradiation device 1 includes an optical fiber 11, a tubular sheath (support member) 12 that supports the optical fiber 11, and an operation member 13. FIG. 2 is a vertical sectional view of the optical fiber 11 and the sheath 12, taken along a longitudinal axis.

The optical fiber 11 is, for example, a single-mode fiber having a cladding diameter of 125 μm. The optical fiber 11 may be a multi-mode fiber or a double cladding fiber.

The sheath 12 is insertable into the surgical-tool channel 2a. The optical fiber 11 extends through the sheath 12 in the longitudinal direction of the sheath 12, and the distal end of the optical fiber 11 protrudes from the distal end of the sheath 12.

A distal end 12a of the sheath 12 is a support section that supports the optical fiber 11 at a position located at a base end side relative to a distal end 11b of the optical fiber 11 with a distance. The inner diameter of the support section 12a is smaller than the inner diameter of other sections of the sheath 12, and is equal to the outer diameter of the optical fiber 11 or slightly larger than the outer diameter of the optical fiber 11. Therefore, at the support section 12a, the position of the optical fiber 11 is fixed in the radial direction. Accordingly, a vibration region 11a of the optical fiber 11 which is disposed at a distal end side relative to the support section 12a and which includes the distal end 11b is supported in a cantilever manner by the sheath 12, and the vibration region 11a can be vibrated in the radial direction of the optical fiber 11 about a part, acting as a fulcrum, of the optical fiber 11 in the support section 12a.

The operation member 13 is a plate-shaped member disposed parallel to the vibration region 11a and is fixed to the sheath 12. The operation member 13 is disposed only at one side of the optical fiber 11 in the radial direction. The distal end of the optical fiber 11 and the operation member 13 have a distance d therebetween in the radial direction of the optical fiber 11. The surface at the optical fiber 11 side of the operation member 13 may be a flat surface or may be a curved surface protruding toward the optical fiber 11.

The operation member 13 and the vibration region 11a disposed outside the sheath 12 are exposed to the outside of the laser irradiation device 1. Therefore, when the laser irradiation device 1 is used within a medium M, the vibration region 11a and the operation member 13 are covered by the medium M. The resonance frequency of the vibration region 11a varies depending on the diameter and length of the vibration region 11a and the medium M surrounding the vibration region 11a. For example, in a case where the vibration region 11a has a core diameter of 272 μm, a cladding diameter of 322 μm, and a length of 45 mm, the resonance frequency is 126 Hz in air and 70 Hz to 80 Hz in water.

The base end of the optical fiber 11 is connected to the laser oscillator 3 by a connection member, such as a connector (not shown). The optical fiber 11 is supplied with a pulsed infrared laser beam L from the laser oscillator 3, and the laser beam L is emitted from the distal end 11b of the optical fiber 11. In the medium M, which is a liquid, the laser beam L is absorbed by the medium M and therefore the temperature of the medium M increases, whereby a bubble B is generated at the distal end 11b (see FIG. 3A to FIG. 4). The medium M is a liquid, such as water, a physiological saline solution, a perfusate, a non-electrolytic solution, or a biological fluid like urine. The bubble B repeatedly forms and vanishes with the pulse frequency of the laser beam L with a synchronous manner. In detail, the bubble B forms and grows while the laser beam L is being emitted, whereas the bubble B rapidly contracts and vanishes when the emission of the laser beam L is stopped.

The operation member 13 is disposed at a position where the bubble B comes into contact therewith, and causes a contraction force generated during contraction of the bubble B to act on the vibration region 11$a$ of the optical fiber 11.

Figure 3A:
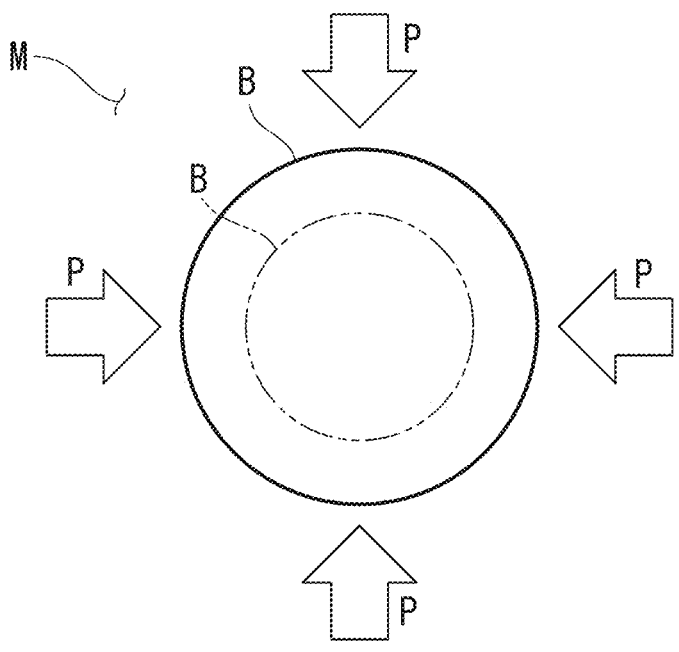
FIG. 3A illustrates isotropic contraction of a bubble when there is no operation member.
Figure 3B:
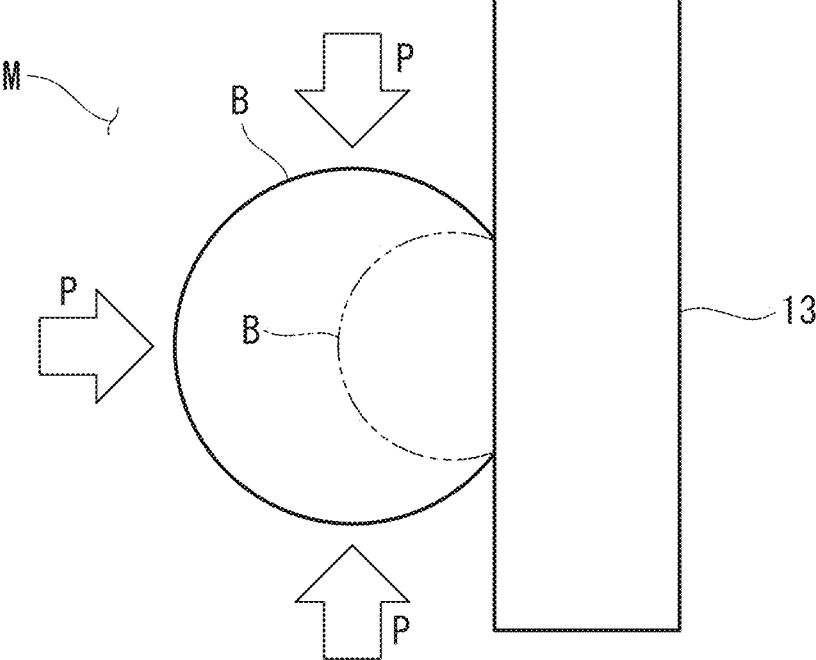
FIG. 3B illustrates non-isotropic contraction of the bubble when there is an operation member, and shows an effect of the operation member.

As shown in FIG. 3A, when there is no object around the bubble B, hydraulic pressure P acts evenly on the bubble B from all directions, thus causing the bubble B to contract isotropically. On other hand, as shown in FIG. 3B, when the operation member 13 exists only at one side of the bubble B such that the bubble B is in contact with the operation member 13, the hydraulic pressure P acts unevenly on the bubble B, thus causing the bubble B to contract toward the operation member 13. Therefore, the operation member 13 can cause the contraction force of the bubble B in the radial direction of the vibration region 11$a$ to act on the distal end 11$b$, so as to vibrate the distal end 11$b$ in the radial direction.

The material of the operation member 13 is not particularly limited. In a case where the surface of the operation member 13 is hydrophobic, the contraction force of the bubble B is larger than a case where the surface is hydrophilic. Therefore, it is preferable that the surface at the optical fiber 11 side of the operation member 13 be hydrophobic.

Figure 4:
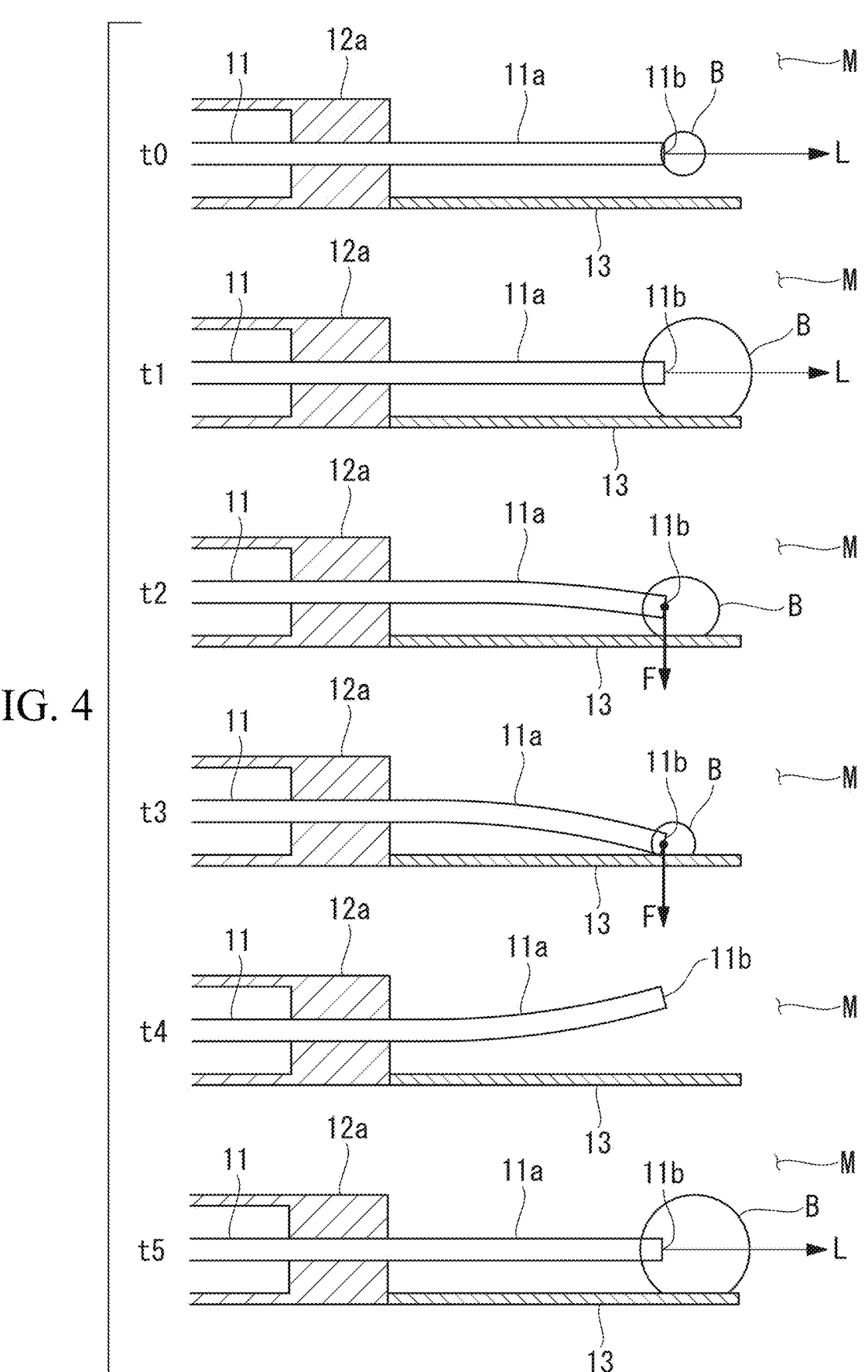
FIG. 4 FIG. 4 illustrates a process of how an optical fiber of the laser irradiation device in FIG. 2 vibrates in accordance with emission of a pulsed laser beam.

FIG. 4 illustrates a process of how the optical fiber 11 vibrates in accordance with generation, contraction, and vanishing of the bubble B as the pulsed laser beam L is emitted.

First, the emission of the laser beam L from the distal end 11$b$ of the optical fiber 11 starts so that the bubble B that is to come into contact with the operation member 13 is generated (t=t0). While the laser beam L is being emitted, the bubble B grows to a predetermined size (t=t1).

Then, when the emission of the laser beam L is stopped, the bubble B contracts, and a contraction force F in the radial direction of the optical fiber 11 toward the operation member 13 acts on the distal end 11$b$ (t=t2). While the bubble B is contracting, the distal end 11$b$ moves in the radial direction toward the operation member 13 in accordance with the contraction force F (t=t3).

Subsequently, when the bubble B vanishes and the contraction force F dissipates, an elastic restoring force of the vibration region 11$a$ causes the distal end 11$b$ to move in the radial direction of the optical fiber 11 toward the opposite side from the operation member 13 (t=t4).

Then, the laser beam L is emitted from the distal end 11$b$ of the optical fiber 11, and the bubble B that is to come into contact with the operation member 13 is generated again (t=t5). The emission start timing of the laser beam L is controlled such that the bubble B grows to the predetermined size when the distal end 11$b$ returns to an initial position as the position when t=t0 and t1.

Subsequently, t2 to t5 are repeated, so that the distal end 11$b$ vibrates in the radial direction, whereby the laser beam L emitted from the distal end 11$b$ is scanned one-dimensionally.

Figure 5A:
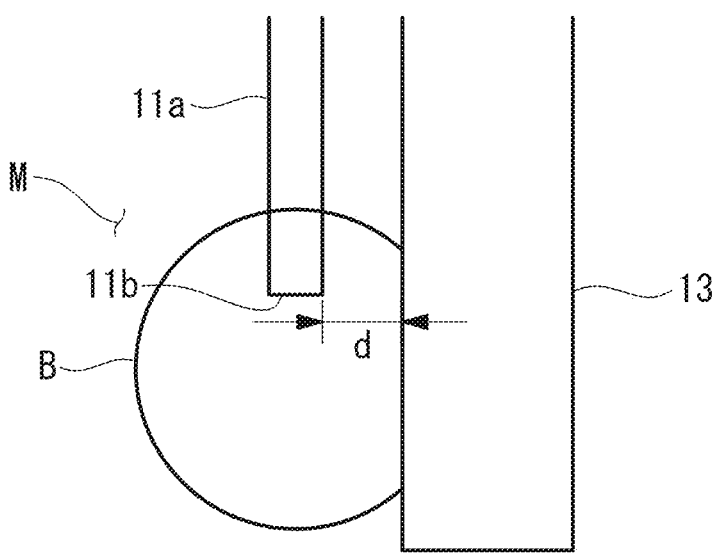
FIG. 5A illustrates a desirable positional relationship between a distal end of the optical fiber and the operation member.
Figure 5B:
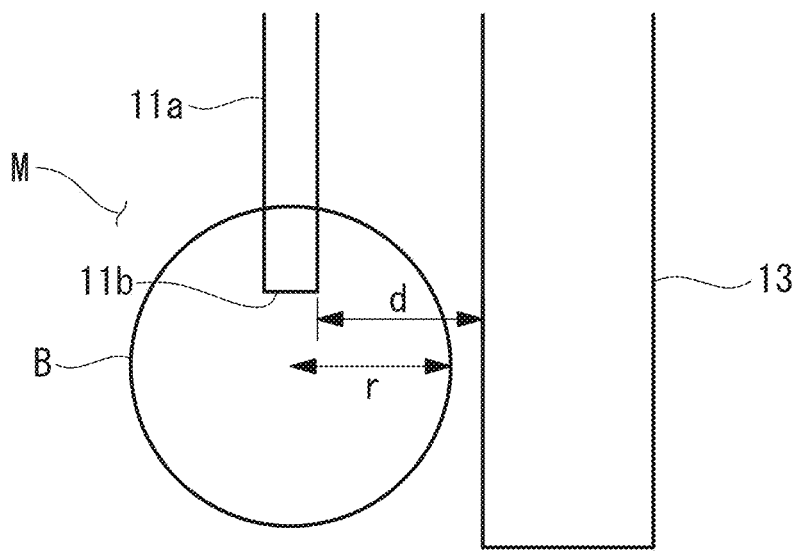
FIG. 5B illustrates an undesirable positional relationship between the distal end of the optical fiber and the operation member.

FIG. 5A and FIG. 5B illustrate the positional relationship between the distal end 11$b$ of the optical fiber 11 and the operation member 13 in the radial direction of the optical fiber 11. As shown in FIG. 5A, in order to cause the bubble B to reliably come into contact with the operation member 13, the distance d between the distal end 11$b$ and the operation member 13 is smaller than or equal to a radius r, as a predetermined upper limit value, of the bubble B. The radius r is the radius of the bubble B generated by the laser beam L when there is no object around the distal end 11$b$. As shown in FIG. 5B, when the distance d is larger than the radius r, the bubble B contracts isotropically, thus making it impossible to cause the contraction force in the radial direction of the optical fiber 11 to act on the distal end 11$b$.

The contraction force varies depending on, for example, the distance d, the diameter of the optical fiber 11, and the irradiation conditions of the laser beam L. If the distance d is too small, the contraction force decreases. An optimal distance d that allows for a sufficient contraction force is determined uniquely in accordance with, for example, the diameter of the optical fiber 11 and the irradiation conditions of the laser beam L.

Figure 6A:
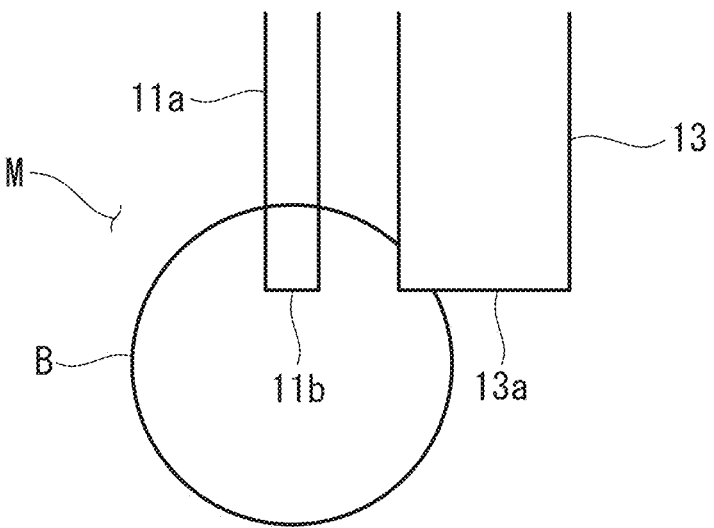
FIG. 6A illustrates a desirable positional relationship between the distal end of the optical fiber and the operation member.
Figure 6B:
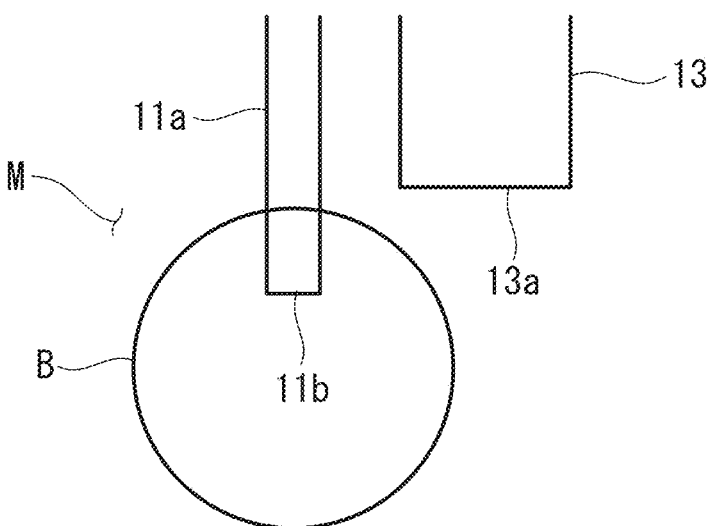
FIG. 6B illustrates an undesirable positional relationship between the distal end of the optical fiber and the operation member.

FIG. 6A and FIG. 6B illustrate the positional relationship between the distal end 11$b$ of the optical fiber 11 and the operation member 13 in the longitudinal direction of the optical fiber 11. As shown in FIG. 6A, in order to cause the bubble B to reliably come into contact with the operation member 13, a distal end 13$a$ of the operation member 13 is disposed at the same position as the distal end 11$b$ or at a position where the distal end 13$a$ protrudes relative to the distal end 11$b$. As shown in FIG. 6B, if the distal end 13$a$ is positioned at a side of the base end relative to the distal end 11$b$, there is a possibility that the bubble B does not come into contact with the operation member 13. In order to apply a greater contraction force to the distal end 11$b$, it is preferable that the contact area between the bubble B and the operation member 13 be larger. Therefore, as shown in FIG. 5A, it is preferable that the distal end of the operation member 13 protrude relative to the distal end 11$b$.

The laser oscillator 3 generates the pulsed laser beam L for treating the treatment target A, and emits the laser beam L. For example, the laser beam L is an infrared beam having a pulse frequency ranging from several Hz to 1000 Hz. The laser oscillator 3 is, for example, a thulium fiber laser, a holmium YAG laser, a thulium YAG laser, an erbium YAG laser, a pulsed dye laser, or a Q-switch Nd YAG laser. The laser oscillator 3 is connected to a foot switch 8. The laser oscillator 3 generates and emits the laser beam L when the foot switch 8 is pressed.

The frequency controller 4 controls the pulse frequency of the laser beam L generated by the laser oscillator 3. In calibration for measuring the resonance frequency of the vibration region 11$a$, the frequency controller 4 changes the pulse frequency generated by the laser oscillator 3. For example, a surgeon inputs a calibration command by using an input device (not shown) and presses the foot switch 8, whereby the calibration is executed.

The movement detector 5 detects movement of the optical fiber 11 that is vibrating. The movement at least includes a vibration amplitude of the distal end 11$b$ of the optical fiber 11, and may further include a vibration frequency. In detail, the movement detector 5 has a vibration detection element 5$a$ fixed to the sheath 12. The vibration detection element 5$a$ is, for example, a vibration sensor, a pressure sensor, or a strain gauge. The vibration of the vibration region 11$a$ is transmitted to the vibration detection element 5$a$ via the support section 12$a$ so as to be detected by the vibration detection element 5$a$. A detection signal output from the vibration detection element 5$a$ changes with the same frequency as the vibration frequency of the vibration region 11$a$. The amplitude of the detection signal increases with increasing vibration amplitude of the distal end 11$b$. The movement detector 5 detects a vibration frequency and a vibration amplitude of the optical fiber 11 based on the vibration frequency and the vibration amplitude of the detection signal.

The resonance determination unit 6 determines whether or not the vibration of the optical fiber 11 resonates with the frequency of the laser beam L based on the movement detected by the movement detector 5 in the calibration. In detail, the resonance determination unit 6 determines that a vibration frequency corresponding to a maximum vibration amplitude is the resonance frequency of the vibration region 11a.

After the resonance determination unit 6 determines the resonance frequency, the frequency controller 4 sets the pulse frequency of the laser beam L generated by the laser oscillator 3 to a frequency equal to the resonance frequency.

The display unit 7 is a display device of any type, such as a liquid crystal display. The display unit 7 displays an endoscopic image acquired by the endoscope 2 and including the distal end 11b of the optical fiber 11 and the treatment target A. Furthermore, the display unit 7 displays the movement of the optical fiber 11 detected by the movement detector 5. For example, the display unit 7 displays a graph indicating the relationship between the pulse frequency and the vibration amplitude acquired in the calibration. The display unit 7 may also display the resonance frequency determined by the resonance determination unit 6.

Next, a laser treatment method using the laser irradiation device 1 and the laser treatment system 100 will be described.

Figure 7:
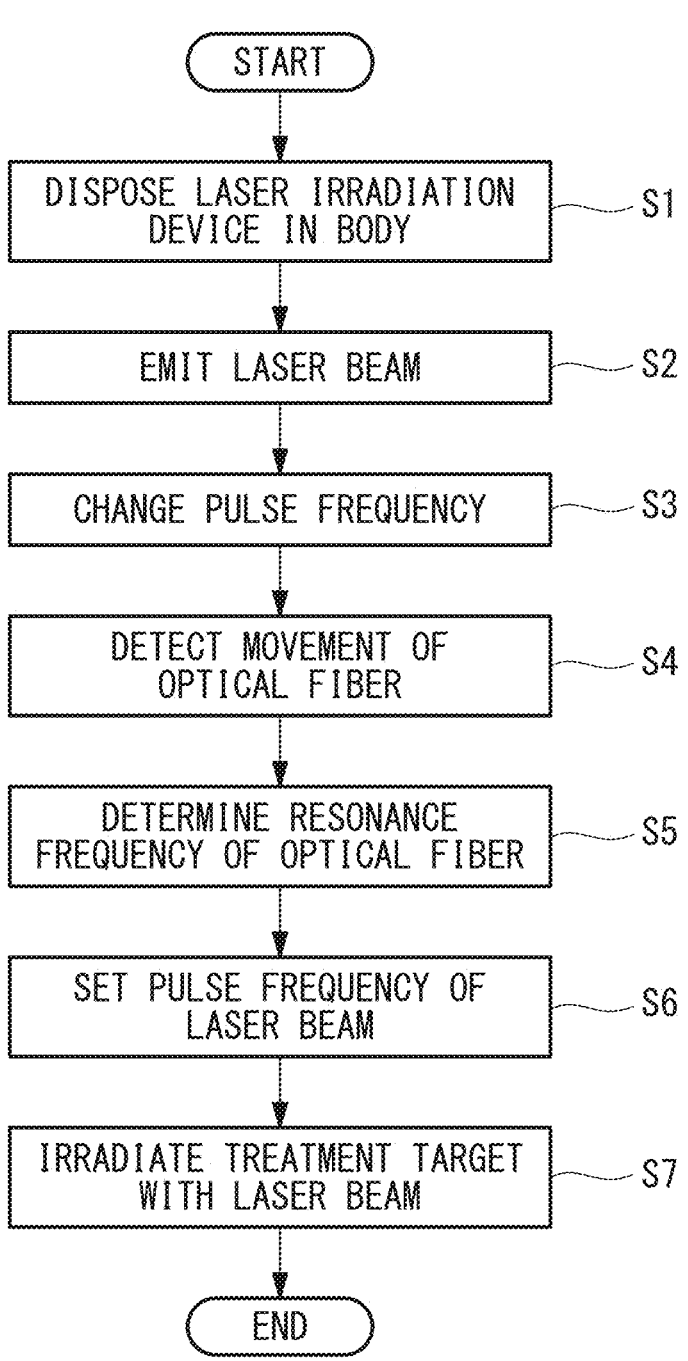
FIG. 7 is a flowchart of a laser treatment method according to an embodiment of the present invention.

As shown in FIG. 7, the laser treatment method includes step S1 for disposing the laser irradiation device 1 within the body, step S2 to step S6 for calibrating the resonance frequency of the vibration region 11a of the optical fiber 11, and step S7 for irradiating the treatment target A with the laser beam L from the laser irradiation device 1 while scanning the laser beam L. Step S2 to step S7 correspond to a laser scanning method according to an embodiment of the present invention.

In step S1, the surgeon inserts the endoscope 2 into the body, such as the ureter, of a patient C, inserts the laser irradiation device 1 into the body via the surgical-tool channel 2a, and disposes the vibration region 11a of the optical fiber 11 outside the endoscope 2. The space surrounding the endoscope 2 and the vibration region 11a is filled with the liquid medium M.

Subsequently, in step S2 to step S6, the surgeon causes the laser treatment system 100 to execute calibration for measuring the resonance frequency of the vibration region 11a. In the calibration, the frequency controller 4 causes the laser oscillator 3 to generate the pulsed laser beam L, so that the pulsed laser beam L is repeatedly emitted from the distal end 11b of the optical fiber 11 (step S2). Moreover, the frequency controller 4 changes the pulse frequency of the laser beam L in a continuous or stepwise fashion (step S3).

Step S2 involves alternately repeating a process for generating and growing the bubble B, which is to come into contact with the distal end 11b and the operation member 13, by means of the laser beam L emitted from the distal end 11b (t=t0, t1, and t5 in FIG. 4) and a process for contracting the bubble B by stopping the emission of the laser beam L from the distal end 11b (t=t2 and t3 in FIG. 4). When the bubble B contracts, the force F acts on the distal end 11b in the radial direction, thus causing the distal end 11b to vibrate in the radial direction.

The distal end 11b vibrates synchronously with the pulse frequency of the laser beam L. The vibration amplitude of the distal end 11b reaches a maximum when the pulse frequency matches the resonance frequency of the vibration region 11a. The movement detector 5 detects movement including the vibration amplitude of the distal end 11b (step S4), and the resonance determination unit 6 determines that the pulse frequency corresponding to the maximum vibration amplitude is the resonance frequency of the vibration region 11a (step S5). The frequency controller 4 sets the pulse frequency of the laser beam L used for treatment to the resonance frequency determined by the resonance determination unit 6 (step S6). In one example, the pulse frequency ranges from 50 Hz to 100 Hz, and preferably ranges from 70 Hz to 80 Hz.

Subsequently, in step S7, the surgeon presses the foot switch 8 to irradiate the treatment target A with the pulsed laser beam L from the distal end 11b of the optical fiber 11, thereby performing a treatment on the treatment target A. Similar to step S2, step S7 involves alternately repeating the process for generating and growing the bubble B, which is to come into contact with the distal end 11b and the operation member 13, by means of the laser beam L emitted from the distal end 11b and the process for contracting the bubble B by stopping the emission of the laser beam L from the distal end 11b. When the bubble B contracts, the force F acts on the distal end 11b in the radial direction, thus causing the distal end 11b to vibrate in the radial direction.

Because the pulse frequency of the laser beam L is equal to the resonance frequency in step S7, the vibration region 11a vibrates with a sufficient amplitude during the irradiation of the laser beam L, and the laser beam L is scanned over the treatment target A. Therefore, as compared with a case where the distal end 11b is stationary, the laser beam L is radiated over a wide range, so that a wide range of the treatment target A can be treated. For example, in a case where the treatment target A is a calculus, a wide range of the calculus A can be crushed while the distal end of the endoscope 2 is maintained at the same position.

Accordingly, the laser irradiation device 1 according to this embodiment utilizes the contraction force of the bubble B generated at the distal end 11b of the optical fiber 11 as a driving force for vibrating the distal end 11b. The bubble B is generated by the treatment laser beam L emitted from the distal end 11b. Specifically, it is not necessary to add an actuator for driving the optical fiber 11 to the optical fiber 11. Thus, a low-profile laser irradiation device 1 can be readily achieved. Moreover, a function for scanning the laser beam L can be added to the laser treatment system 100 without increasing the power consumption of the laser treatment system 100.

In a case where an electromagnetic or piezoelectric actuator is used for vibrating the optical fiber 11, an electromagnetic field generated by the actuator may have an adverse effect on the endoscopic image. In this embodiment, the treatment laser beam L is an infrared beam, therefore an adverse effect on the endoscopic image can be prevented.

Because the resonance frequency of the vibration region 11a varies between the air and the liquid medium M, it is difficult to accurately predict the resonance frequency of the vibration region 11a in the usage environment. Furthermore, in order to obtain a vibration amplitude of the distal end 11b required for scanning the laser beam L in the liquid medium M, it is important to cause the vibration region 11a to resonate by matching the pulse frequency with the resonance frequency of the vibration region 11a. If the pulse frequency is different from the resonance frequency, it is difficult to obtain a sufficient vibration amplitude of the vibration region 11a due to the viscosity resistance of the medium M. According to this embodiment, the resonance frequency can be calibrated in a state where the vibration region 11*a* is disposed in the treatment environment, so that the resonance frequency of the vibration region 11*a* can be accurately measured in the treatment environment. Accordingly, during the treatment, the vibration region 11*a* can be vibrated with the maximum vibration amplitude, so that a maximum scanning range of the laser beam L can be obtained.

Figure 8A:
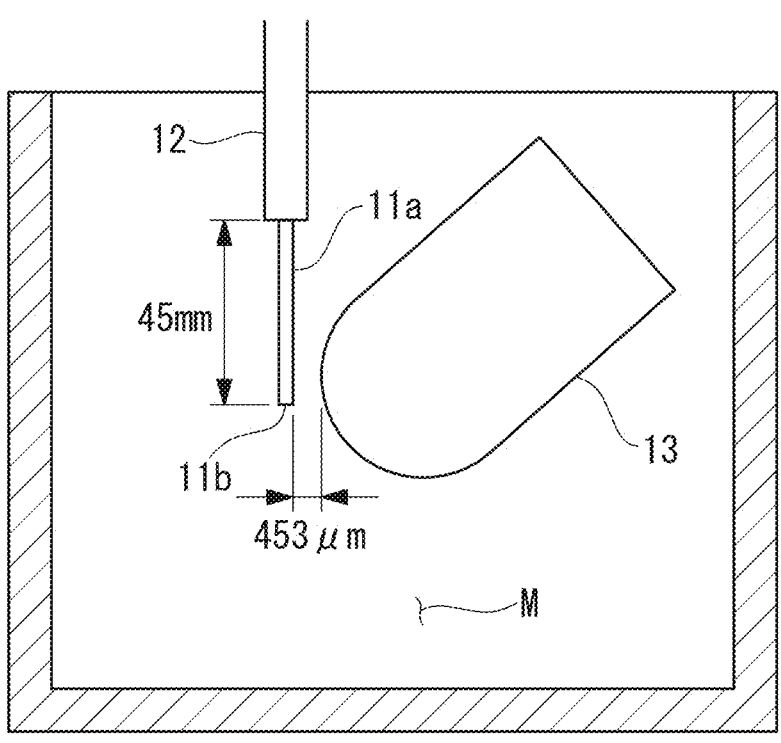
FIG. 8A illustrates experimental conditions in a practical example of the present invention.
Figure 8B:
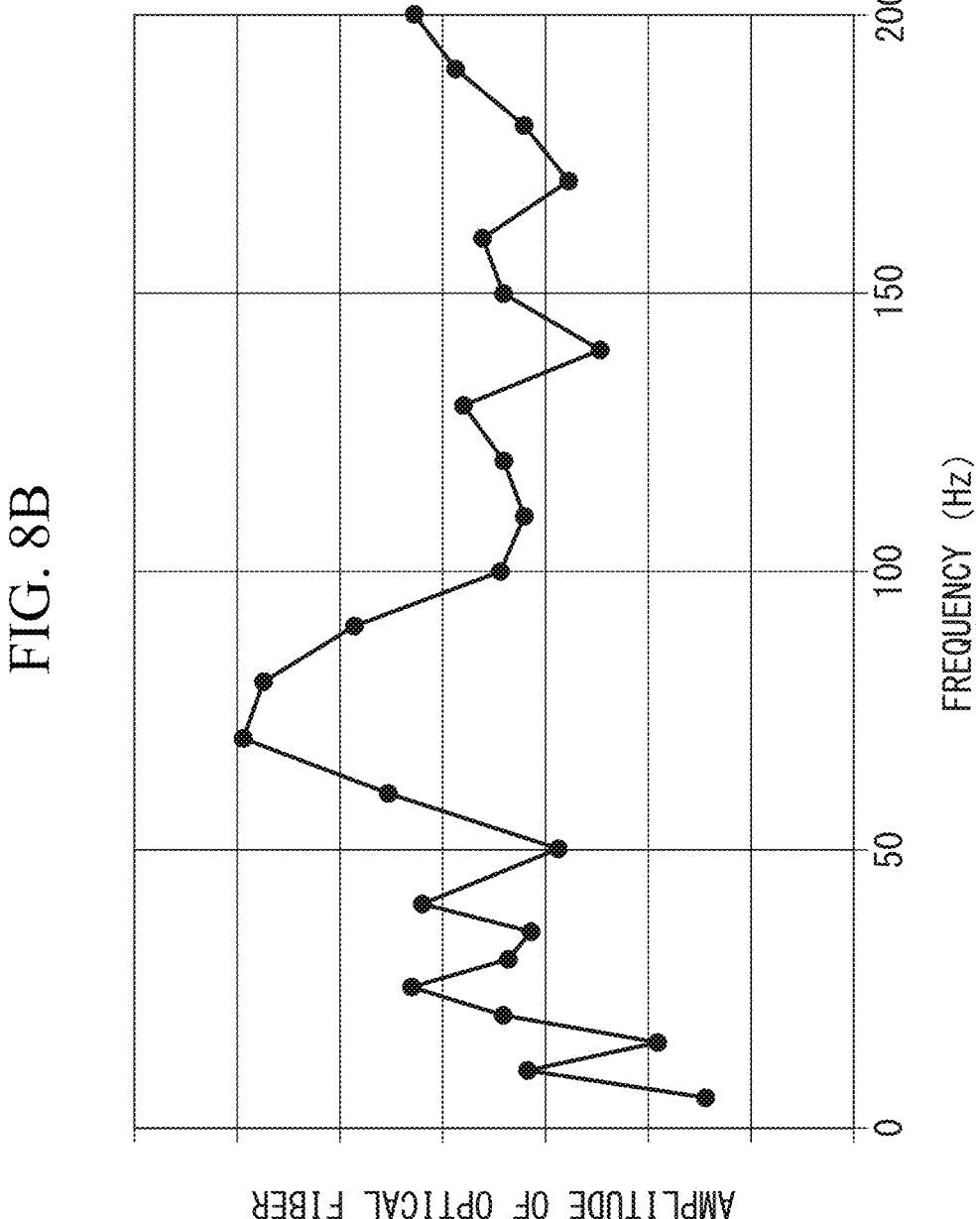
FIG. 8B is a graph illustrating experimental results regarding the practical example of the present invention and indicating a relationship between a pulse frequency and a vibration amplitude of the distal end of the optical fiber.

FIG. 8A and FIG. 8B illustrate a practical example for calibrating the resonance frequency of the optical fiber 11.

As shown in FIG. 8A, the vibration region 11*a* of the optical fiber 11 and the operation member 13 are disposed in water serving as the medium M, the pulsed laser beam L is supplied from the laser oscillator 3 to the optical fiber 11, and the vibration amplitude of the distal end 11*b* of the optical fiber 11 is measured while the pulse frequency of the laser beam L is changed.

The vibration region 11*a* has a length of 45 mm, and the distance d between the distal end 11*b* and the operation member 13 is set to 453 μm. The optical fiber 11 used is MedTech HLFDBX0270C, Dornier (having a core diameter of 270 μm and manufactured by Olympus Corporation). The operation member 13 used is a tube. The laser oscillator 3 used is a thulium fiber laser (TLR-50/500-QCW AC manufactured by IPG Photonics Corporation). The irradiation conditions for the laser beam L include 500 W, 0.4 ms, 0.2 J, and 5 Hz to 200 Hz. A move of the vibrating optical fiber 11 is captured at 250 fps by using a high-speed camera (FASTCAM-1024PCI manufactured by Photron Limited).

The procedure of the experiment is as follows.

(1) The pulse frequency is changed in units of 5 Hz from 5 Hz to 35 Hz, and the laser beam L is radiated every 0.5 seconds.

(2) The pulse frequency is changed in units of 10 Hz from 40 Hz to 200 Hz, and the laser beam L is radiated every 0.5 seconds.

(3) A maximum amplitude of the distal end 11*b* at the operation member 13 side is measured for each pulse frequency from the move.

FIG. 8B illustrates the results of the above experiment, and has an abscissa axis indicating the pulse frequency and an ordinate axis indicating the vibration amplitude of the distal end 11*b*. As shown in FIG. 8B, it is confirmed that the vibration amplitude is at a maximum at 70 Hz and 80 Hz, and that the resonance frequency of the vibration region 11*a* ranges between 70 Hz and 80 Hz. It is also confirmed from the move that vibration begins as a result of the vibration region 11*a* being drawn toward the operation member 13 during contraction of the bubble B.

Figure 9A:
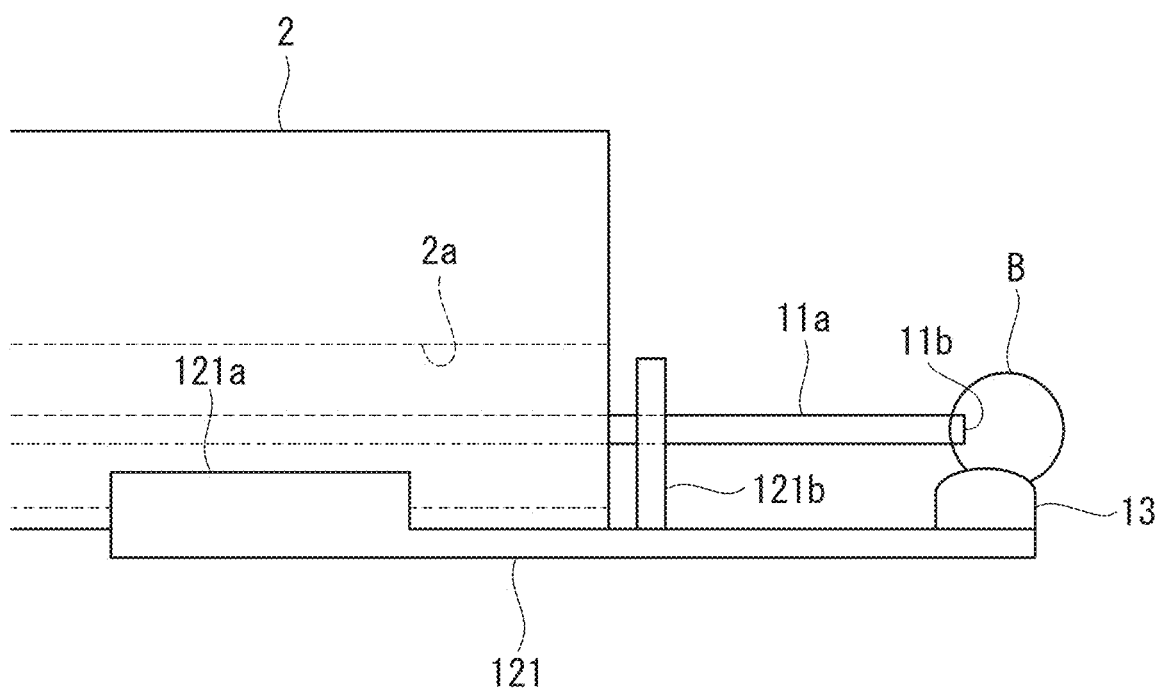
FIG. 9A illustrates a configuration of a part of a laser irradiation device according to another embodiment of the present invention.
Figure 9B:
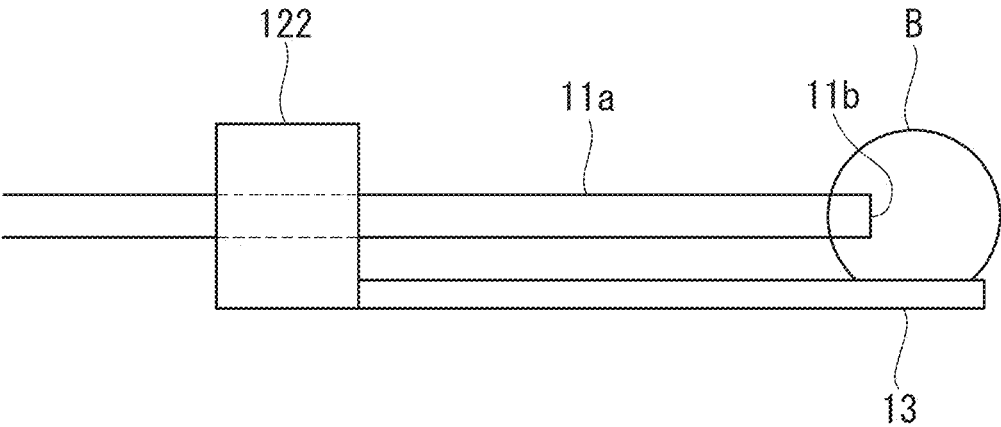
FIG. 9B illustrates a configuration of a part of a laser irradiation device according to another embodiment of the present invention.

In the above embodiment, the laser irradiation device 1 includes the sheath 12 as a support member that accommodates the optical fiber 11, and the sheath 12 is inserted together with the optical fiber 11 into the surgical-tool channel 2*a*. Alternatively, the configuration of the support member is not limited to this and may be changed to any form so long as the support member can support the optical fiber 11 in a cantilever manner about a fulcrum. FIG. 9A and FIG. 9B illustrate other examples of the support member.

A support member 121 in FIG. 9A is of an external type attached to the outer surface of the distal end of the endoscope 2. The support member 121 is a long member extending in the longitudinal direction of the endoscope 2 and has an attachment section 121*a* attached to a side surface of the distal end of the endoscope 2 and a support section 121*b* that supports the optical fiber 11. The operation member 13 is fixed to the distal end of the support member 121. The support section 121*b* is a plate-shaped member disposed in front of the distal end surface of the endoscope 2 and has a hole through which the optical fiber 11 extends. A segment of the optical fiber 11 in the support section 121*b* acts as a fulcrum. In order to set the distance between the distal end 11*b* of the optical fiber 11 and the operation member 13 to an appropriate distance, the operation member 13 protrudes toward a side of the optical fiber 11 from the support member 121.

A support member 122 in FIG. 9B is an annular or tubular member fixed to the outer surface of the optical fiber 11. The optical fiber 11 extends through the support member 122, and a segment of the optical fiber 11 in the support member 121 acts as a fulcrum.

In the above embodiment, the movement detector 5 detects the movement of the vibration region 11*a* by using the vibration detection element 5*a*. Alternatively, the specific configuration of the movement detector 5 is not limited to this, and the movement may be detected by using other means.

Figure 10A:
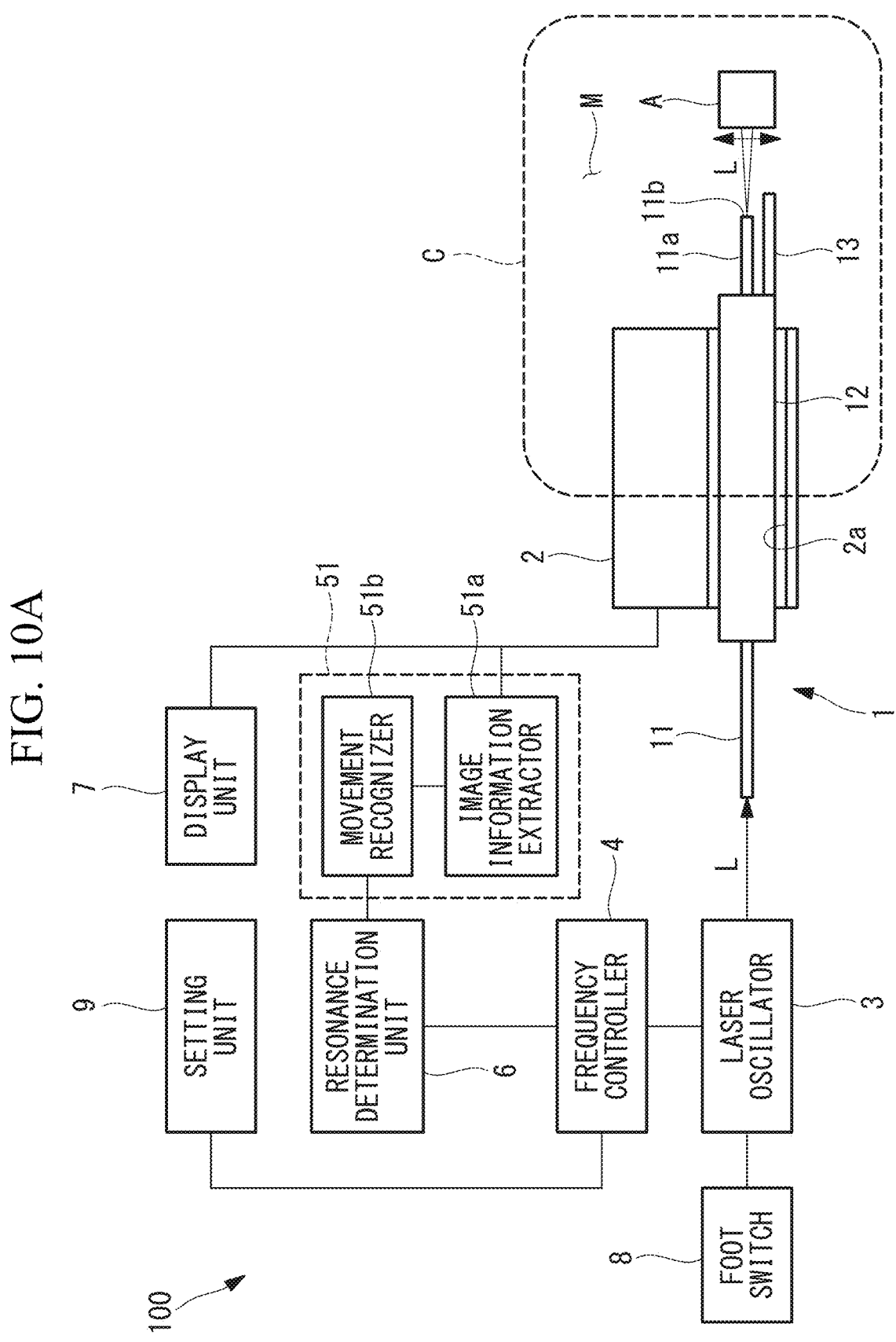
FIG. 10A illustrates an overall configuration of a laser treatment system according to another embodiment of the present invention.
Figure 10B:
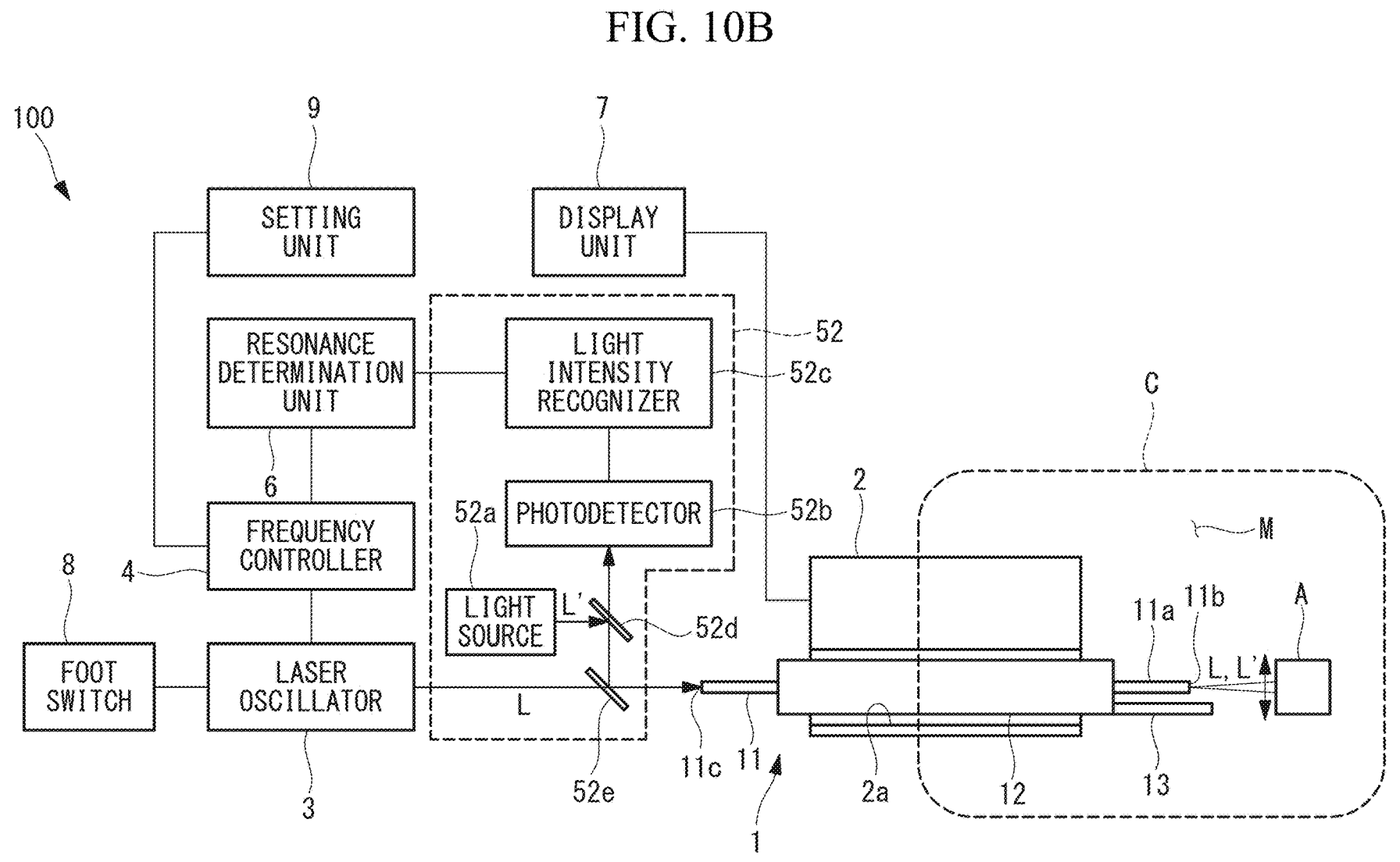

FIG. 10A and FIG. 10B illustrate other examples of the movement detector 5.

A movement detector 51 of the laser treatment system 100 in FIG. 10A detects movement based on an endoscopic image acquired by the endoscope 2 during calibration and including the distal end 11*b*. The movement detector 51 includes an image information extractor 51*a* and a movement recognizer 51*b*.

The image information extractor 51*a* extracts image information related to the vibration of the distal end 11*b* from the endoscopic image. For example, the image information includes the distal end 11*b* of the optical fiber 11, the bubble B, or reflection light of a guide beam. The guide beam is radiated onto an object, such as the treatment target A, from the distal end 11*b* and is reflected by the object.

The movement recognizer 51*b* recognizes a vibration amplitude and a vibration frequency as the movement of the distal end 11*b* based on a change in the image information (e.g., a positional change).

A movement detector 52 of the laser treatment system 100 in FIG. 10B detects the movement based on a measurement beam L' returning from an object, such as the treatment target A, via the optical fiber 11. The movement detector 52 includes a light source 52*a*, a photodetector 52*b*, and a light intensity recognizer 52*c*.

The light source 52*a* emits a laser beam as the measurement beam L'. The measurement beam L' is combined with the laser beam L by mirrors 52*d* and 52*e*, enters the base end of the optical fiber 11, and enters the photodetector 52*b* via the distal end 11*b* of the optical fiber 11, the treatment target A, the distal end 11*b*, a base end 11*c*, the mirror 52*e*, and the mirror 52*d*.

When the distal end 11*b* is stationary, the intensity of the measurement beam L' entering the photodetector 52*b* is fixed. When the distal end 11*b* is vibrating, the intensity of the measurement beam L' entering the photodetector 52*b* changes in accordance with the vibration amplitude and the vibration frequency of the distal end 11*b*.

The light intensity recognizer 52*c* recognizes the vibration amplitude and the vibration frequency as the movement of the vibration region 11*a* based on the intensity of the measurement beam L' detected by the photodetector 52*b*.

In the above embodiment, as shown in FIG. 10A and FIG. 10B, the laser treatment system 100 may further include a setting unit 9 used by the surgeon for manually setting the pulse frequency of the laser beam L. The surgeon can observe an endoscopic image displayed on the display unit 7 during calibration, determine the pulse frequency when the vibration amplitude of the distal end 11*b* is at a maximum, and set the determined pulse frequency in the frequency controller 4 by using the setting unit 9.

Figure 11:
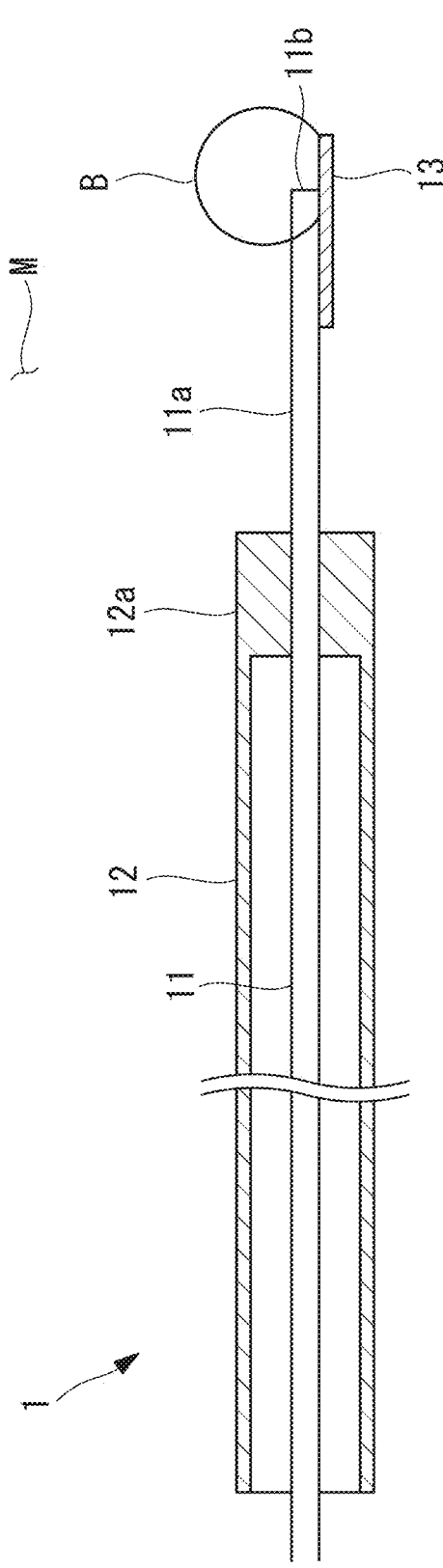
FIG. 11 illustrates a configuration of a laser irradiation device according to another embodiment of the present invention.

In the above embodiment, the operation member 13 is disposed at a position located away from the distal end 11*b* of the optical fiber 11 in the radial direction by the distance d. Alternatively, as shown in FIG. 11, the operation member 13 may be in contact with the distal end 11*b* of the optical fiber 11 and be fixed to the distal end of the optical fiber 11. Specifically, the distance d may be zero. In this case, the operation member 13 is not fixed to the support member 12 and vibrates together with the distal end 11*b*.

The operation member 13 of the laser irradiation device 1 in FIG. 11 causes a water jet stream generated during contraction of the bubble B to act on the vibration region 11*a* of the optical fiber 11.

Figure 12A:
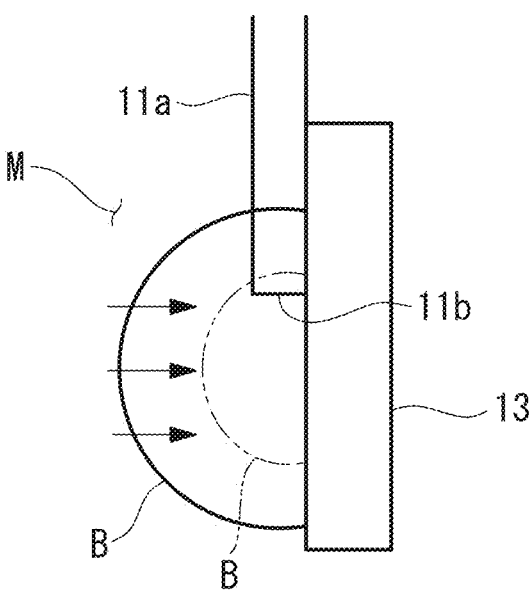
FIG. 12A illustrates non-isotropic contraction of the bubble and an effect of the operation member.

As shown in FIG. 12A, in a case where the operation member 13 exists only at one side of the bubble B and the bubble B is in contact with the operation member 13, hydraulic pressure acts unevenly on the bubble B, thus causing the bubble B to contract toward the operation member 13. During the contraction of the bubble B, a water jet stream (see arrows in FIG. 12A) in the radial direction of the vibration region 11*a* is generated toward the operation member 13, and the operation member 13 receives the water jet stream. Therefore, as shown in FIG. 12B, the operation member 13 can cause the vibration region 11*a* to vibrate in the radial direction.

Figure 12B:
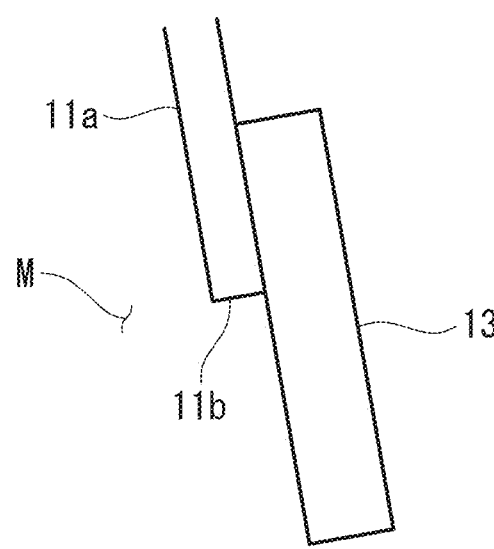
FIG. 12B illustrates an effect of the operation member.

In order to generate a stronger water jet stream during the contraction of the bubble B, it is preferable that the surface at the optical fiber 11 side of the operation member 13 in FIG. 11 to FIG. 12B be hydrophobic.

Figure 13:
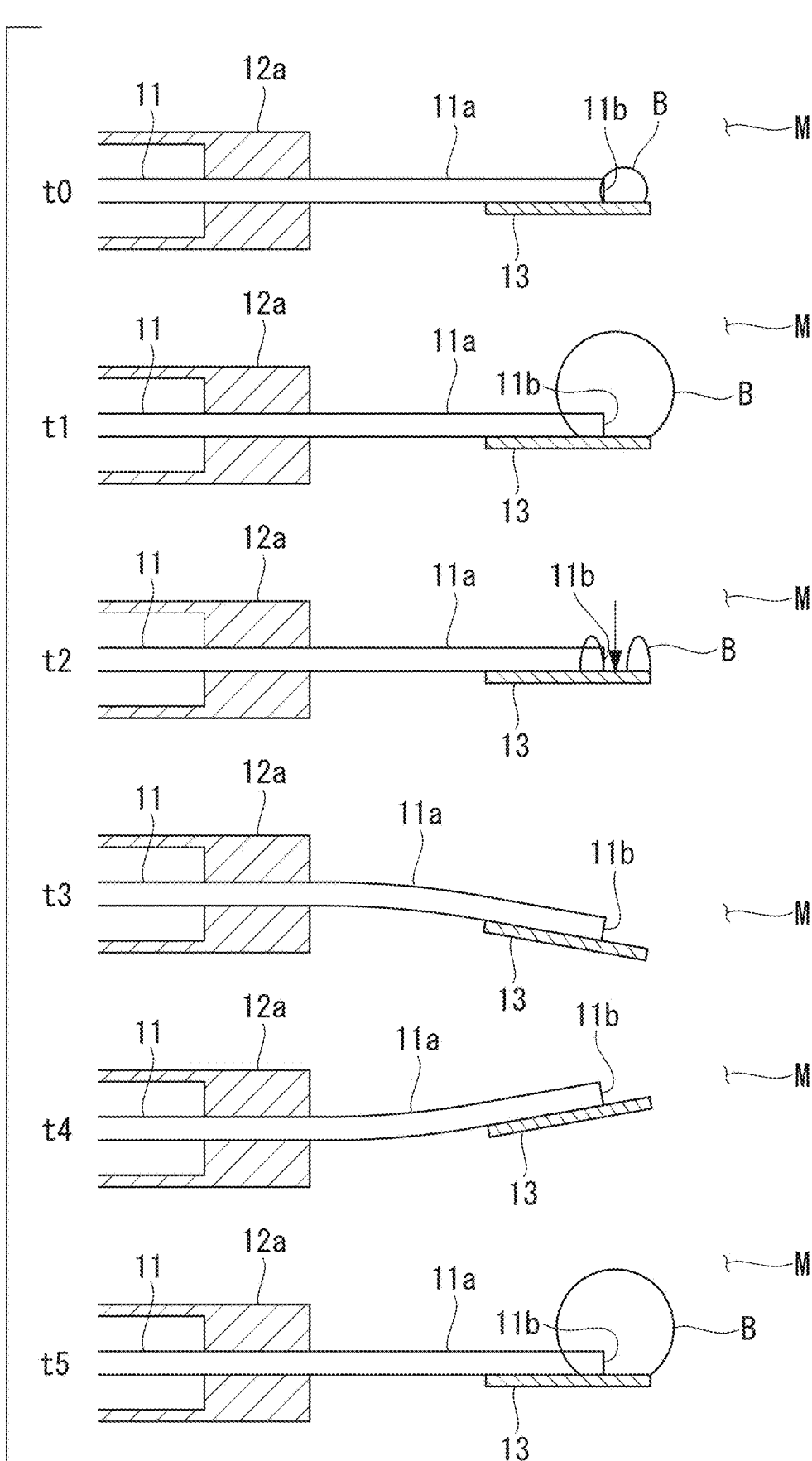
FIG. 13 illustrates a process of how the optical fiber of the laser irradiation device in FIG. 11 vibrates in accordance with emission of a pulsed laser beam.

FIG. 13 illustrates a process of how the optical fiber 11 vibrates in accordance with generation, contraction, and vanishing of the bubble B as the pulsed laser beam L is emitted.

First, the emission of the laser beam L from the distal end 11*b* of the optical fiber 11 starts so that the bubble B that is to come into contact with the operation member 13 is generated (t=t0). While the laser beam L is being emitted, the bubble B grows to a predetermined size (t=t1).

Then, when the emission of the laser beam L is stopped, the bubble B contracts, and the water jet stream (see the arrows) in the radial direction of the optical fiber 11 toward the operation member 13 is generated (t=t2). While the bubble B is contracting, the operation member 13 and the distal end 11*b* move together in the radial direction in accordance with the water jet stream (t=t3).

Subsequently, when the bubble B vanishes and the contraction force F dissipates, an elastic restoring force of the vibration region 11*a* causes the distal end 11*b* and the operation member 13 to move together in the radial direction toward the opposite side (t=t4).

Then, the laser beam L is emitted from the distal end 11*b* of the optical fiber 11, so that the bubble B that is to come into contact with the operation member 13 is generated again (t=t5). The emission start timing of the laser beam L is controlled such that the bubble B grows to the predetermined size when the distal end 11*b* returns to the initial position serving as the position when t=t0 and t1.

Subsequently, t2 to t5 are repeated, so that the distal end 11*b* vibrates in the radial direction, whereby the laser beam L emitted from the distal end 11*b* is scanned one-dimensionally.

As an alternative to the above embodiment in which the laser beam L is scanned one-dimensionally in accordance with one-dimensional vibration of the distal end 11*b* of the optical fiber 11, the laser beam L may be scanned two-dimensionally in accordance with two-dimensional vibration of the distal end 11*b* of the optical fiber 11.

Figure 14A:
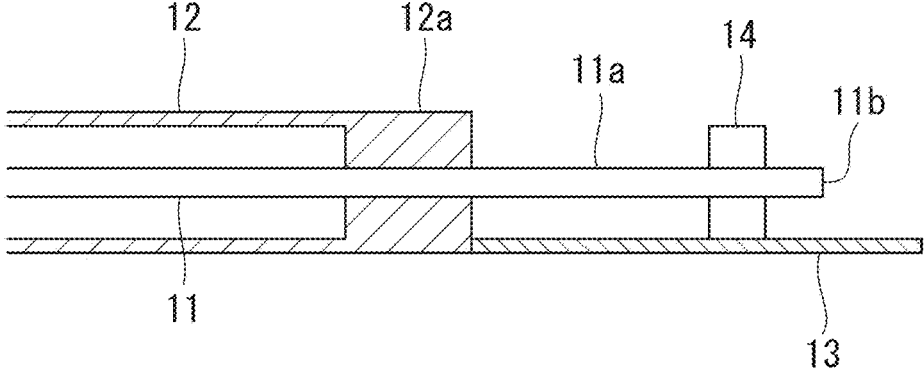
FIG. 14A is a vertical sectional view a part of a configuration of a laser irradiation device according to another embodiment of the present invention.
Figure 14B:
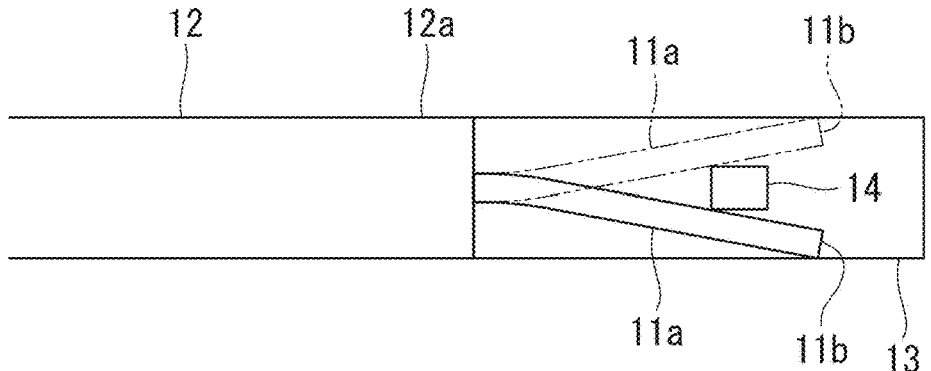
FIG. 14B is a plan view of the laser irradiation device in FIG. 14A.
Figure 14C:
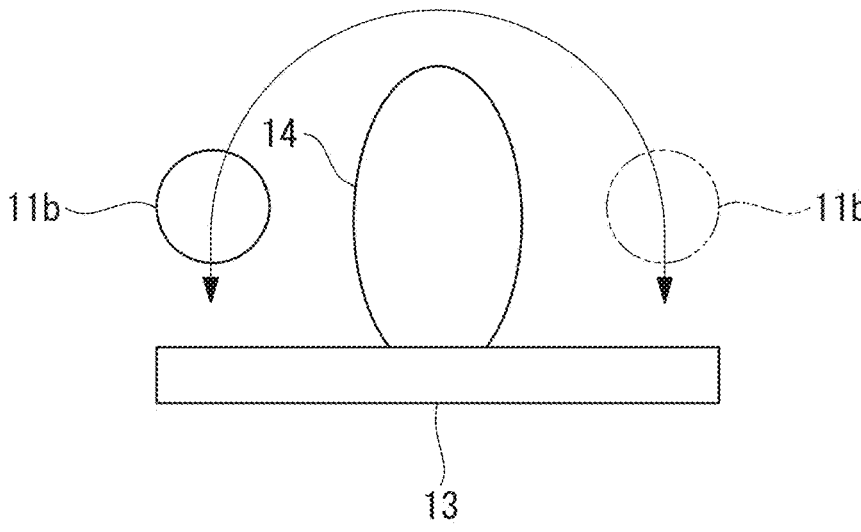
FIG. 14C is a front view of the laser irradiation device in FIG. 14A.

FIG. 14A to FIG. 14C illustrate a configuration example of the laser irradiation device 1 that vibrates the distal end 11*b* of the optical fiber 11 two-dimensionally. FIG. 14A is a vertical sectional view of the optical fiber 11 and the sheath 12, taken along the longitudinal axis. FIG. 14B is a plan view of the laser irradiation device in FIG. 14A, as viewed from above. FIG. 14C is a front view of the laser irradiation device in FIG. 14A, as viewed along the longitudinal axis from the distal end.

The surface at the optical fiber 11 side of the operation member 13 has a displacement member 14 that is fixed thereto and that protrudes toward a side of the optical fiber 11 from the operation member 13 and that is provided for displacing the vibration region 11*a* in a direction intersecting the direction in which the distal end 11*b* is moved by the contraction force of the bubble B. Although the displacement member 14 shown in FIG. 14C has a substantially elliptical cross-sectional shape, the shape of the displacement member 14 is not limited thereto and may be changed, where appropriate. For example, the displacement member 14 may have a triangular cross-sectional shape.

In FIG. 14C, the bubble B is generated when the distal end 11*b* is disposed at the left of the displacement member 14. When the distal end 11*b* moves rightward in accordance with the contraction force of the bubble B, the distal end 11*b* also moves in the vertical direction by moving over the displacement member 14. Therefore, the laser beam L is scanned two-dimensionally along a circular-arc trajectory.

Subsequently, the bubble B is generated when the distal end 11*b* reaches the right side of the displacement member 14. When the distal end 11*b* moves leftward in accordance with the contraction force of the bubble B, the distal end 11*b* also moves in the vertical direction by moving over the displacement member 14. Therefore, the laser beam L is scanned two-dimensionally along a circular-arc trajectory.

Figure 15A:
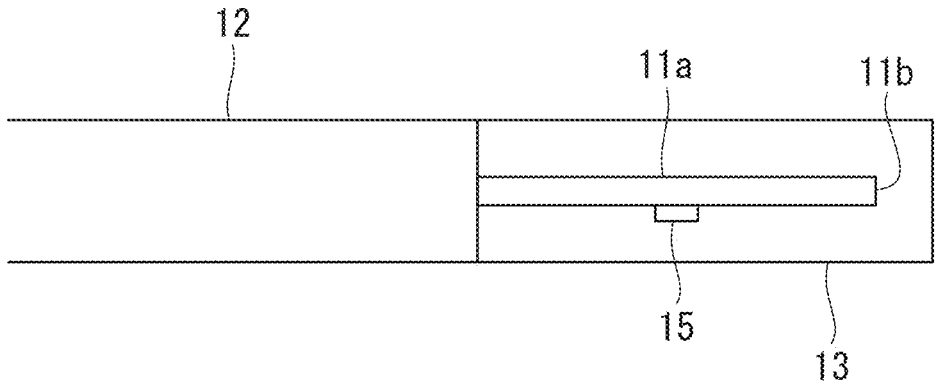
FIG. 15A is a plan view illustrating a configuration of a laser irradiation device according to another embodiment of the present invention.
Figure 15B:
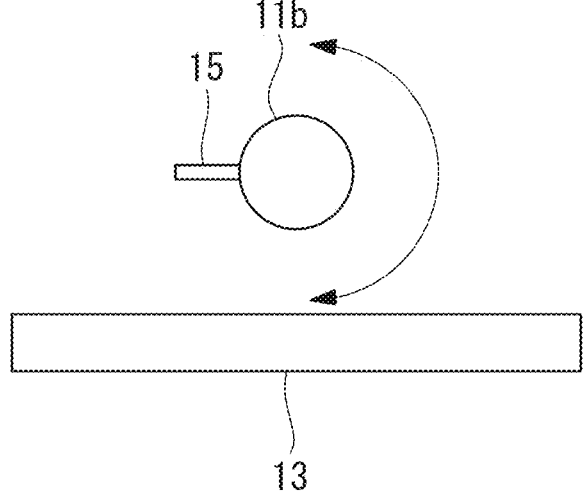
FIG. 15B is a front view of the laser irradiation device in FIG. 15A.

FIG. 15A and FIG. 15B illustrate another configuration example of the laser irradiation device 1 that vibrates the distal end 11*b* of the optical fiber 11 two-dimensionally. FIG. 15A is a plan view of the laser irradiation device, as viewed from above. FIG. 15B is a front view of the laser irradiation device in FIG. 15A, as viewed along the longitudinal axis from the distal end.

A fin 15 is fixed to a side surface of the vibration region 11*a*. In FIG. 15B, when the vibration region 11*a* vibrates in the horizontal direction in accordance with the contraction force of the bubble B or the water jet stream, the fin 15 receives resistance of the medium M, so that the distal end 11*b* also moves in the vertical direction. Accordingly, the distal end 11*b* is moved two-dimensionally, as indicated by an arrow, so that the laser beam L can be scanned two-dimensionally.

The laser treatment system 100 includes at least one processor, such as a central processing unit, and memory units, such as a RAM (random access memory) and a ROM (read-only memory). At least some of the aforementioned functions of the frequency controller 4, the movement detectors 5, 51, and 52, and the resonance determination unit 6 are implemented by the processor executing a program stored in the memory. Some of the functions of the frequency controller 4, the movement detectors 5, 51, and 52, and the resonance determination unit 6 may be implemented by, for example, a dedicated logic circuit.

The present disclosure is advantageous in that a laser beam can be scanned in a liquid medium without having to add an actuator for driving an optical fiber to the optical fiber and without increasing the power consumption.

REFERENCE SIGNS LIST

1 laser irradiation device
2 endoscope (image acquisition unit)
3 laser oscillator
4 frequency controller
5, 51, 52 movement detector
6 resonance determination unit
7 display unit
11 optical fiber
11*a* vibration region
11*b* distal end
12, 121, 122 support member
13 operation member
100 laser treatment system
A treatment target
B bubble
L laser beam
M medium

The invention claimed is:

1. A laser scanning method for scanning a laser beam emitted from a distal end of an optical fiber disposed in a liquid medium, the laser scanning method comprising:

emitting the laser beam from the distal end of the optical fiber in the liquid medium, wherein the emitting the laser beam is effective to generate a bubble at the distal end of the optical fiber that contacts an operation member, the operation member being disposed within the liquid medium, adjacent to the distal end of the optical fiber, and only at one side of the distal end of the optical fiber in a radial direction of the optical fiber;

stopping the emission of the laser beam from the distal end of the optical fiber, wherein the stopping the emission of the laser beam is effective to:

cause the bubble to shrink non-isotropically toward the operation member based on a contraction force generated by the contact between the bubble and the operation member effective to draw the optical fiber towards the operation member; and cause the optical fiber to move away from the operation member by a restoring force of the optical fiber when the bubble vanishes and the contraction force dissipates; and repeating the emitting and the stopping at a pulse frequency.

2. The laser scanning method according to claim 1, wherein the laser beam is configured for treating a treatment target.

3. The laser scanning method according to claim 1, further comprising:

changing the pulse frequency to one or more other pulse frequencies; and detecting movement of the optical fiber at the pulse frequency and each of the pulse frequencies, the movement including at least a vibration amplitude of the distal end of the optical fiber.

4. The laser scanning method according to claim 3, further comprising:

determining a resonance frequency of the optical fiber in the medium based on the movement of the optical fiber; and setting the pulse frequency to the resonance frequency.

5. The laser scanning method according to claim 4, wherein the pulse frequencies range from 50 Hz to 100 Hz.

6. A laser irradiation device comprising:

a laser oscillator configured to supply a pulsed laser beam to a distal end of an optical fiber in a liquid medium; and a controller configured to cause the laser oscillator to supply the pulsed laser beam, wherein the causing the laser oscillator to supply the pulsed laser beam is effective to, when the optical fiber is in the liquid medium:

for each pulse of the pulsed laser beam, generate a bubble at the distal end of the optical fiber that contacts an operation member disposed adjacent to the distal end of the optical fiber and disposed only at one side of the distal end of the optical fiber in a radial direction of the optical fiber; and for each period between pulses of the pulsed laser beam:

cause the bubble to shrink non-isotropically toward the operation member based on a contraction force generated by the contact between the bubble and the operation member effective to draw the optical fiber towards the operation member; and cause the optical fiber to move away from the operation member by a restoring force of the optical fiber when the bubble vanishes and the contraction force dissipates.

7. The laser irradiation device according to claim 6, wherein the pulsed laser beam is configured for treating a treatment target.

8. The laser irradiation device according to claim 6, further comprising a movement detector configured to detect movement of the optical fiber, wherein the controller is further configured to:

change a pulse frequency of the pulsed laser beam to one or more pulse frequencies; and determine respective vibration amplitudes of the distal end of the optical fiber at the pulse frequencies based on information received from the movement detector.

9. The laser irradiation device according to claim 8, wherein the controller is further configured to:

determine a resonance frequency of the optical fiber in the medium based on the vibration amplitudes of the optical fiber at the pulse frequencies; and set the pulse frequency of the pulsed laser beam to the resonance frequency.

10. The laser irradiation device according to claim 9, wherein the pulse frequencies of the laser beam range from 50 Hz to 100 Hz.

11. A laser treatment system comprising:

an optical fiber configured to be disposed in a liquid medium;

an operation member configured to be disposed in the liquid medium, disposed adjacent to a distal end of the optical fiber, and disposed only at one side of the distal end of the optical fiber in a radial direction of the optical fiber;

a laser oscillator configured to supply a pulsed laser beam to the optical fiber for emission from the distal end of the optical fiber; and a controller configured to cause the laser oscillator to supply the pulsed laser beam, wherein the causing the laser oscillator to supply the pulsed laser beam is effective to, when the optical fiber is in the liquid medium:

for each pulse of the pulsed laser beam, generate a bubble at the distal end of the optical fiber that contacts the operation member; and for each period between pulses of the pulsed laser beam:

cause the bubble to shrink non-isotropically toward the operation member based on a contraction force generated by the contact between the bubble and the operation member effective to draw the optical fiber towards the operation member; and cause the optical fiber to move away from the operation member by a restoring force of the optical fiber when the bubble vanishes and the contraction force dissipates.

12. The laser treatment system according to claim 11, wherein the pulsed laser beam is configured for treating a treatment target.

13. The laser treatment system according to claim 11, further comprising a movement detector configured to detect movement of the optical fiber, wherein the controller is further configured to:

change a pulse frequency of the pulsed laser beam to one or more pulse frequencies; and determine respective vibration amplitudes of the distal end of the optical fiber at the pulse frequencies based on information received from the movement detector.

14. The laser treatment system according to claim 13, wherein the controller is further configured to:

determine a resonance frequency of the optical fiber in the medium based on the vibration amplitudes of the optical fiber at the pulse frequencies; and set the pulse frequency of the pulsed laser beam to the resonance frequency.

15. The laser treatment system according to claim 13, further comprising:

an image acquisition unit configured to acquire one or more images including the distal end of the optical fiber and a treatment target; and a display unit configured to display the images and the movement of the optical fiber detected by the movement detector.

16

16. A laser treatment method comprising:

disposing a distal end of an optical fiber and an operation member in a liquid medium, the operation member being adjacent to the distal end of the optical fiber and only at one side of the distal end of the optical fiber in a radial direction of the optical fiber;

emitting a laser beam from the distal end of the optical fiber effective to generate a bubble at the distal end of the optical fiber that contacts the operation member;

stopping the emission of the laser beam from the distal end of the optical fiber effective to:

cause the bubble to shrink non-isotropically toward the operation member based on a contraction force generated by the contact between the bubble and the operation member effective to draw the optical fiber towards the operation member; and cause the optical fiber to move away from the operation member by a restoring force of the optical fiber when the bubble vanishes and the contraction force dissipates; and repeating the emitting and the stopping at a pulse frequency.

17. The laser treatment method according to claim 16, further comprising:

changing the pulse frequency to one or more other pulse frequencies; and detecting movement of the optical fiber at the pulse frequency and each of the pulse frequencies, the movement including at least a vibration amplitude of the distal end of the optical fiber.

18. The laser treatment method according to claim 17, further comprising:

determining a resonance frequency of the optical fiber in the medium based on the movement of the optical fiber; and setting the pulse frequency to the resonance frequency.

19. The laser treatment method according to claim 18, wherein the pulse frequencies range from 50 Hz to 100 Hz.

20. The laser treatment system according to claim 11, wherein the operation member is plate-shaped.

* * * * *